United States Patent [19]

Tang

[11] 4,384,146
[45] May 17, 1983

[54] PROCESS FOR BUTANEDIOLS

[75] Inventor: Sunny C. Tang, Katy, Tex.

[73] Assignee: Shell Oil Company, Houston, Tex.

[21] Appl. No.: 103,658

[22] Filed: Dec. 14, 1979

[51] Int. Cl.$^3$ ...................... C07C 31/20; C07C 179/06
[52] U.S. Cl. ..................................... 568/861; 568/561
[58] Field of Search ............................... 568/861, 561

[56] References Cited

U.S. PATENT DOCUMENTS 3,896,051  7/1975  Mabuchi et al. .................... 568/861

OTHER PUBLICATIONS

Kharash et al., "J. Org. Chem.", vol. 18 (1953), pp. 322–327.
Basolo et al., "Catalysis", Progress in Research (1973), pp. 177 to 185.

*Primary Examiner*—J. E. Evans

[57] ABSTRACT

1,4- and 1,2-butanediols are selectively produced by reacting 1,3-butadiene with tert-butyl hydroperoxide in the presence of a cobalt on silica catalyst, followed by catalytic hydrogenation of the di(tert-butylperoxy)butenes obtained thereby.

11 Claims, No Drawings

PROCESS FOR BUTANEDIOLS

BACKGROUND OF THE INVENTION

This invention relates to a two step process for the selective production of 1,4- and 1,2-butanediol. More particularly, this invention is directed toward a process which comprises reacting 1,3-butadiene with tert-butyl hydroperoxide in the presence of a supported cobalt catalyst, followed by catalytic hydrogenation of the di(tert-butylperoxy) butenes obtained thereby.

Butadiene is widely available as a co-product of steam-cracking olefins plants or from the dehydrogenation of butylenes from refineries. Methods of converting butadiene to other commercially valuable compounds, such as butanediols, are thus of interest. The more valuable butanediol is 1,4-butanediol, which finds applications as a solvent, an intermediate for the production of tetrahydrofuran and a component for a variety of polyurethanes, plastics and resins. Classical Reppe chemistry is currently used for the commercial production of 1,4-butanediol from acetylene and formaldehyde. Due to the cost and explosive tendency of acetylene, an alternative route to 1,4-butanediol is desirable. With the instant invention, a simple and effective alternative process for the production of butanediols from a butadiene feedstock has been devised. The process affords both high yields and selectivities to butanediols, while favoring the production of the more valuable 1,4-butanediol.

Various paths leading to 1,4-butanediol from 1,3-butadiene have been demonstrated; they include acetoxylation (British Pat. No. 1,170,222), oxidation (U.S. Pat. No. 3,238,225), hydroboration (U.S. Pat. No. 3,060,244) and hydrogenation of a butadiene-oxygen copolymer (German Pat. No. 2,232,699 and U.S. Pat. No. 2,879,306). In contrast, the instant process reacts tert-butyl hydroperoxide (TBHP) with 1,3-butadiene to form a mixture of di(tert-butylperoxy)butenes, which are subsequently hydrogenated to butanediols.

Kharasch et al, J. Org. Chem., 18, 322 (1953), disclose a similar process for the production of di(tert-butylperoxy)butenes using a homogeneous cobalt napthenate catalyst, but without the use of a solvent. The use of such a liquid catalyst renders separation of the products from the catalyst difficult and results in a very long reaction time; these problems are avoided by the present heterogeneous cobalt catalyst. Kharasch et al also disclose a subsequent hydrogenation step using a palladium on charcoal catalyst, although the yields or selectivities obtained are not made clear.

Kharasch and Fono, J. Org. Chem., 24, 72 (1959), disclose the reaction of hydroperoxides with olefins using cobaltous salts as catalysts. In the additional presence of a one-electron oxidizing agent, an alkylperoxy olefin (containing only one peroxy grouping) is formed.

Milas et al, J. Am. Chem. Soc., 68, 205 (1946), disclose the hydrogenation of di-tert-butylperoxide over a Raney nickel catalyst to yield tert-butyl alcohol.

In Kochi, J. Am. Chem. Soc., 84, 2785 (1962), TBHP and butadiene react in the presence of copper and/or iron-containing catalysts to form tert-butoxybutenylacetates or butoxymethoxybutenes, neither of which contain peroxy groupings.

SUMMARY OF THE INVENTION

A process has now been discovered for the production of butane-diols which comprises:
(a) reacting 1,3-butadiene with tert-butyl hydroperoxide in the presence of a cobalt on silica catalyst; and
(b) catalytically hydrogenating the di(tert-butylperoxy)butenes obtained thereby.

The process offers the advantages of heterogeneous catalysis, faster reaction rates, high yields and selectivities to butanediols and a favorable ratio of the more valuable 1,4-butanediol to 1,2-butanediol in the product mix.

The process itself comprises reacting 1,3-butadiene with TBHP to form 1,4-di(tert-butylperoxy)butene-2 and 3,4-di(tert-butylperoxy)butene-1, represented by formulae (I) and (II), respectively:

(I) $(CH_3)_3C-O-O-CH_2-HC=CH-CH_2-O-O-C(CH_3)_3$

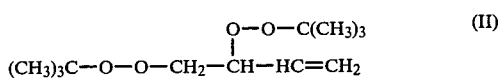

(II) 
$$\underset{(CH_3)_3C-O-O-CH_2-CH-HC=CH_2}{\overset{O-O-C(CH_3)_3}{|}}$$

The di(tert-butylperoxy)butene (TBPB) intermediates are then catalytically hydrogenated to butanediols. The major by-product of the overall process reaction is tert-butanol.

DESCRIPTION OF THE PREFERRED EMBODIMENTS

The reaction of the 1,3-butadiene with TBHP, referred to as the peroxidation step, is carried out in the presence of a heterogeneous cobalt on silica catalyst. The cobalt on the support is present in its unreduced (non-metallic) state, i.e., having a positive oxidation state. Preferably, the catalyst will be calcined prior to use in the process; it is believed that calcination binds the cobalt more tightly to the support, thereby preventing significant leaching of the metal into the reaction solution. Use of a silica support for the catalyst has been found to result in high selectivities to the desired di(tert-butylperoxy) butenes, while maintaining a satisfactory molar ratio of 1,4-versus 1,2-addition. The type of silica support used is not critical, although silicas with surface areas of at least 10 square meters per gram are preferred. The support in all cases should be inert to reaction conditions. The catalyst for the peroxidation step is suitably prepared by mixing an aqueous or an alcoholic solution of a cobalt salt, e.g., cobalt acetate in methanol, with the support, followed by removal of the remaining aqueous or alcoholic solution, followed preferably by calcination. Amounts of cobalt used are not critical, so long as a catalytically effective amount of the metal is present. The amount of the cobalt used may affect the reaction rates however. Very high loadings of cobalt on the silica support are not preferred, for reasons of economy and maximizing the activity of the catalyst. Preferably, from about 10% to about 30% by weight of cobalt will be deposited on the support, more preferably from about 15% to about 25% by weight of cobalt. The molar ratio of cobalt to reactant TBHP used is suitably from 0.0001 to 1.0, with from 0.001 to 0.1 being more preferred. Substantially all of the cobalt catalyst is suitably removed from the reaction mixture prior to the second step, in order to avoid the possibility that it may be reduced under the hydrogenation conditions described hereafter. If desired, the cobalt catalyst may then be regenerated by heating in the presence of oxygen.

In the peroxidation step, an excess of the 1,3-butadiene reactant is suitably present, so that the reaction rate and catalyst activity is monitored by measurement of the TBHP. Since water is believed to act as a free radical trap, both the butadiene and TBHP reactants are preferably dried prior to use in the process. The peroxidation step is generally conducted at temperatures below room temperature; this aids in preventing the evaporation of the volatile butadiene reactant and is believed to improve the selectivity to the desired products. Thus, temperatures from $-20°$ C. to $25°$ C. are preferred, with $-15°$ C. to $10°$ C. more preferred. There are no particular pressure requirements for the peroxidation step, although atmospheric pressure is most convenient. Pressures above atmospheric can be helpful in controlling volatilization of the butadiene and are preferred when the reaction is run at temperatures exceeding the preferred ranges given above. The reaction is allowed sufficient time for completion; for example, when temperatures from $-15°$ C. to $10°$ C. are used, the reaction is typically allowed to proceed for 3 to 12 hours.

The peroxidation step is optionally and preferably carried out in a solvent medium. In general, the use of an appropriate solvent improves the conversion and/or ratio of 1,4- versus 1,2-addition. As discussed above, water may have an adverse effect on the free radical reaction which occurs, so that non-aqueous solvents are preferred. Suitable solvents include liquid aromatics, alcohols, paraffins and ethers (cyclic or acyclic). The term liquid solvent is used to denote a solvent which remains a liquid at the reaction temperatures specified herein. Preferred solvents include isopropanol, tert-butanol, toluene and tetrahydrofuran; of these, toluene affords the best result for the peroxidation step but must be removed prior to the second step due to the possibility of its hydrogenation. The more preferred solvents for the peroxidation step are those which are not susceptible to hydrogenation under the conditions of the subsequent catalytic hydrogenation step, so as to eliminate the need to change solvents between the two steps. The more preferred solvents thus include isopropanol, tert-butanol and tetrahydrofuran. The most preferred solvent is tert-butanol, since it is a co-product of both the peroxidation and the hydrogenation steps and its use would obviate obtaining a solvent mixture. The tert-butanol may also be converted to TBHP and recycled, as will be more fully discussed below.

The yields of the desired di(tert-butylperoxy)butenes of formulae (I) and (II) obtained by the peroxidation step of this invention are excellent with, under optimum conditions using a toluene solvent, conversions (based on TBHP) of over 97%, selectivities of over 82% and molar ratios of 1,4- versus 1,2-addition of over 3.0 being obtained. If a solvent is used which may be retained for the subsequent hydrogenation step, then again under optimum conditions, conversions of over 83%, selectivities of over 87% and molar ratios of 1,4- versus 1,2-addition of over 2.0 are obtained.

The second step of the process of this invention is the catalytic hydrogenation of the desired products of the peroxidation step, namely di(tert-butylperoxy)butenes of formulae (I) and (II) above. The term "hydrogenation", as used herein, denotes the simultaneous peroxo-linkage hydrogenolysis and double bond saturation of the di(tert-butylperoxy)butenes. The catalyst used for this step may be selected from a wide variety of known hydrogenation catalysts, both supported and unsupported, many of which are commercially available. Suitable catalysts include, for example, platinum oxide, platinum on carbon, platinum black, rhenium on alumina, rhenium on carbon, rhenium metal, ruthenium on alumina, ruthenium on carbon, rhodium on carbon, rhodium on alumina, rhodium on silica, palladium on carbon, palladium on barium sulfate, palladium on calcium carbonate, palladium black, palladium oxide, copper chromite, copper oxide on alumina, Raney copper, copper carbonate on silica, Raney nickel, nickel on kieselguhr, nickel on carbon, Raney iron and cobalt on kieselguhr. Preferred catalysts include Raney nickel and palladium on carbon, with Raney nickel being more preferred. The support, if used, should be inert to reaction conditions. The catalyst used in this step of the process is preferably reduced. Many of the suitable catalysts listed are conveniently reduced in situ, that is, reduced during the hydrogenation reaction under the reaction conditions described hereafter. Other hydrogenation catalysts may be reduced in a conventional manner or, in the case of commercially available catalysts, reduced according to the manufacturer's specifications. The amounts of metal used are not critical, so long as a catalytically effective amount of the metal is present. The amount of catalyst used may affect the hydrogenation rate however. Preferably the molar ratio of catalyst to reactant TBPB is from 0.0001 to 1.0, with from 0.001 to 0.1 more preferred.

The hydrogenation step is conducted in a conventional manner and under relatively mild conditions. For example, this step is suitably conducted at temperatures of from about $20°$ C. to about $300°$ C., with about $20°$ C. to about $130°$ C. preferred. The hydrogenation rate is generally temperature dependent. The reaction is also suitably run at elevated pressures, e.g. about 200 to about 1300 pounds per square inch (psi) hydrogen is typical. The hydrogenation is frequently done in two stages: a first stage done at a lower temperature and pressure followed by a second stage with higher temperature and pressure. For example, use of a Raney nickel catalyst at room temperature and 200 psi hydrogen for one hour followed by $130°$ C. and 1300 psi hydrogen for 4 hours affords good results. Further adjustment of temperature, pressure, amounts and types of catalyst, reaction times and other parameters are believed to be apparent to one skilled in conventional catalytic hydrogenation.

The catalytic hydrogenation is optionally and preferably carried out in a solvent medium. As seen above, many of the solvents useful for the peroxidation step may be retained in the reaction vessel and also used for the hydrogenation step, so long as such solvents are not susceptible to hydrogenation under the conditions outlined. The preferred solvents are tert-butanol and tetrahydrofuran, with tert-butanol being more preferred since it is a co-product of both steps of the process, a suitable solvent for both steps and since it may be converted to TBHP and recycled. Examples of such suitable methods for the conversion of tert-butanol to TBHP include the reaction of tert-butanol in sulfuric acid with hydrogen peroxide, as described in Milas et al, J. Am. Chem. Soc. 68, 205 (1946), and U.S. Pat. No. 2,573,947.

In addition to tert-butanol and the desired butanediols, other by-products which may appear in minor amounts from the hydrogenation step include gamma-butyrolactone and various high boiling materials. If desired, the gamma-butyrolactone may be isolated and converted into 1,4-butanediol in accordance with known procedures, for example, those disclosed in Chemical Abstracts, Vol. 78, Nos. 3677x and 3735q (1973). The reaction product may be purified by conventional means such as extraction, chromatography, or distillation. The more valuable 1,4-butanediol may be separated from the 1,2-butanediol by fractional distillation.

The yields of butanediols obtained by the second step of the process of this invention are excellent with, under optimum conditions, conversion of the di(tert-butylperoxy)butenes of over 95% with selectivities over 92% being obtained. Further, a molar ratio of 1,4-butane-diol to 1,2-butanediol in excess of 1.4 may be obtained in conjunction with the optimum yields stated.

The invention is illustrated further in the following examples, which are not to be construed as limiting its scope. In the examples, the 1,3-butadiene used was reagent grade and was dried over Drierite and a molecular sieve prior to use. The tert-butyl hydroperoxide was dried over a molecular sieve and analyzed to be 98.5±0.05% TBHP. All solvents used were reagent grade.

In examples where the results for the peroxidation step are shown, the conversion percentage is based on TBHP analysis. The selectivity and molar ratio of 1,4- versus 1,2-addition are calculated by reducing the reaction mixture from the peroxidation step with zinc powder in glacial acetic acid to obtain 1,4- and 1,2-butenediols, which are subsequently analyzed using vapor phase chromatography. The metal loading on the peroxidation catalyst is expressed in terms of weight-percent of cobalt on the support.

In examples where the results for the hydrogenation step are shown, the conversion percentage is based on di(tert-butylperoxy)butene analysis. The selectivity and molar ratio of 1,4- versus 1,2-butane-diols are calculated by analyzing the reaction mixture from the hydrogenation step directly, using gas chromatography-mass spectroscopy and vapor phase chromatography.

EXAMPLE I

A calcined cobalt on silica (20%) peroxidation catalyst was prepared by dry impregnation of Davison ID silica gel (14–30 mesh) with an aqueous solution of cobalt acetate (85% saturated) at 110° F. The amount of solution used was based on 90% of the pore volume of the dry silica. The dry impregnation was repeated two additional times. The catalyst was then dried and calcined with air at 570° C., and used in granular form.

EXAMPLE II

A peroxidation reaction between 1,3-butadiene and TBHP was carried out in a 250 ml 3-neck round-bottomed flask equipped with a condenser and a drying tube containing Drierite and molecular sieves. The flask was charged with 300 mg of a cobalt on silica (20%) catalyst prepared as in Example I. Subsequently 20.0 g (0.37 moles) of 1,3-butadiene were condensed in the flask and the mixture magnetically stirred at −15° C. Using a Sage Model 255-2 syringe pump, 5.0 ml (0.049 moles) of TBHP were added dropwise over a 3 hour period. The reaction mixture was allowed to stir overnight and slowly warmed to 10° C. The results are shown below in Table I and compared to results of a similar experiment utilizing a calcined cobalt on silica catalyst with a lower metal loading (15%).

TABLE I

REACTION OF 1,3-BUTADIENE WITH TBHP USING CO/SiO$_2$ CATALYSTS

| Example | Catalyst | Conversion of TBHP | Selectivity[1] | Molar Ratio of 1,4 vs 1,2-Addition |
|---|---|---|---|---|
| IIa | Co/SiO$_2$ (15%) | 64.3% | 84.4% | 1.26 |
| IIb | Co/SiO$_2$ (20%) | 69.8% | 88.5% | 2.49 |

[1]Selectivity to 1,4- and 1,2-butenediols

EXAMPLE III

In this series of experiments, 1,3-butadiene and TBHP were reacted as in Example II using a variety of supported cobalt catalysts. The results are shown in Table II. Example IIa is repeated for purposes of comparison.

TABLE II

REACTION OF 1,3-BUTADIENE WITH TBHP USING SUPPORTED CATALYSTS

| Example | Catalyst | Conversion of TBHP | Selectivity[1] | Molar Ratio of 1,4 vs 1,2-Addition |
|---|---|---|---|---|
| IIa | Co/SiO$_2$(15%) | 64.3% | 84.4% | 1.26 |
| IIIa | Co(ac)$_2$/SiO$_2$(15%)[2] | — | 83.8% | 0.80 |
| IIIb | Co(ac)$_2$/Al$_2$O$_3$(15%)[3] | 31.8% | 27.3% | 1.63 |
| IIIc | Co(ac)$_2$/Zeolite(4A)(15%)[3] | 79.9% | 80.6% | 0.42 |

[1]Selectivity to 1,4- and 1,2-butenediols
[2]Prepared as in Example I, with the exception that a 15% metal loading was used and the catalyst was not calcined.
[3]Not according to the invention.

EXAMPLE IV

A series of experiments were conducted according to the procedure outlined in Example II, but with 20 ml of the indicated solvent also charged to the reaction flask prior to the addition of the butadiene. The solvents tested were tetrahydrofuran (THF), tert-butanol (TBA), isopropanol (IPA) and toluene, and the catalyst used was prepared as in Example I. The results are shown in Table III.

TABLE III

REACTION OF 1,3-BUTADIENE WITH TBHP: SOLVENT EFFECTS

| Example | Catalyst | Solvent | Conversion of TBHP | Selectivity[1] | Molar Ratio of 1,4 vs 1,2-Addition |
|---|---|---|---|---|---|
| IVa | Co/SiO$_2$ (20%) | THF | 80.9% | 77.5% | 2.99 |
| IVb | Co/SiO$_2$ (20%) | TBA | 83.3% | 87.0% | 2.05 |
| IVc | Co/SiO$_2$ (20%) | IPA | 92.4% | 68.3% | 1.70 |
| IVd | Co/SiO$_2$ (20%) | Toluene | 97.5% | 82.3% | 3.15 |

[1]Selectivity to 1,4- and 1,2-butenediols.

EXAMPLE V

In order to determine the degree of leaching into the liquid phase of a catalyst prepared as in Example I, product solutions from Examples IVa and IVb were analyzed for cobalt by atomic absorption. A blank solution of tetrahydrofuran was similarly tested as a control. The results given in Table IV demonstrate a low level of catalyst leaching even though the reactions were carried out in magnetically stirred reactors.

TABLE IV

REACTION OF 1,3-BUTADIENE WITH TBHP: COBALT ANALYSIS

| Example | Solvent | Co(mg/l) | Corrected for Blank (mg/l) | Solvent Density | PPM[1] |
|---|---|---|---|---|---|
| Va | THF | 0.48 | 0.45 | 0.8892 | 0.51 |
| Vb | TBA | 0.29 | 0.26 | 0.7809 | 0.33 |
| Vc | THF[2] | 0.03 | — | — | — |

[1] Catalyst leaching in parts per million
[2] Blank (no catalyst present)

EXAMPLES VI-XIII

In this series of experiments, the product solutions from Examples IVa and IVb (using the indicated solvents) were hydrogenated over wet Raney nickel (1.5 g) or palladium on charcoal (10%; 0.5 g). In a typical reaction (Example VIII), 25.0 ml of the product solution and 1.5 g of wet Raney nickel in tetrahydrofuran were added to a 100 ml stainless-steel, magnetically stirred, glass lined autoclave. The reaction mixture was purged with nitrogen gas. The hydrogenation was then carried out for one hour at room temperature (RT) and 200 psi hydrogen, followed by 4 hours at 130° C. and 1300 psi hydrogen. The mixture was cooled to room temperature, filtered and analyzed. Results are shown in Table V.

TABLE V

HYDROGENATION OF PRODUCT SOLUTIONS

| Example | Catalyst | Solvent | Reaction Conditions Temp (°C.) | Pressure (psi H$_2$) | Time (hr) | Conversion | Selectivity to 1,2- and 1,4-Butanediols | Molar Ratio of 1,4 vs 1,2-Butanediol |
|---|---|---|---|---|---|---|---|---|
| VI | Raney Ni | TBA | RT | 200 | 1 | 96.0% | 92.3% | 1.42 |
|  |  |  | 130 | 1300 | 4 |  |  |  |
| VII | Raney Ni | TBA | RT | 200 | 1 | 99.2% | 92.7% | 1.46 |
|  |  |  | 130 | 1300 | 7 |  |  |  |
| VIII | Raney Ni | THF | RT | 200 | 1 | 78.7% | 70.4% | 1.40 |
|  |  |  | 130 | 1300 | 4 |  |  |  |
| IX | Raney Ni | THF | RT | 200 | 1 | 80.2% | 71.1% | 1.44 |
|  |  |  | 130 | 1300 | 9.5 |  |  |  |
| X | Pd/C | TBA | 100 | 800 | 4 | 41.1% | 59.8% | 2.66 |
| XI | Pd/C | TBA | 100 | 800 | 4 | 67.4% | 40.0% | 0.77 |
|  |  |  | 130 | 1300 | 3 |  |  |  |
| XII | Pd/C | THF | 100 | 800 | 4 | 74.4% | 40.5% | 26.6 |
| XIII | Pd/C | THF | 100 | 800 | 4 | 71.0% | 18.3% | 4.79 |
|  |  |  | 130 | 1300 | 1.5 |  |  |  |

What is claimed is:

1. A process for the production of 1,4-butanediol and 1,2-butanediol which comprises:
    (a) reacting 1,3-butadiene with tert-butyl hydroperoxide in an added reaction solvent selected from the class consisting of liquid aromatics, alcohols, paraffins and cyclic or acyclic ethers, in the presence of an unreduced cobalt on silica catalyst, to obtain a peroxidation reaction mixture comprising 1,4-di(tert-butylperoxy)butene-2 and 3,4-di(tert-butylperoxy)butene-1;
    (b) catalytically hydrogenating the 1,4-di(tert-butylperoxy)butene-2 and the 3,4-di(tert-butylperoxy)-butene-1 to obtain 1,4-butanediol and 1,2-butanediol.

2. The process of claim 1 wherein the hydrogenation catalyst is Raney nickel.

3. The process of claim 1, wherein the reaction of 1,3-butadiene with tert-butyl hydroperoxide is carried out in a tetrahydrofuran, tert-butanol, isopropanol or toluene solvent.

4. The process of claim 1 wherein the catalytic hydrogenation is carried out in a tetrahydrofuran or tert-butanol solvent.

5. The process of claim 1 wherein the reaction of 1,3-butadiene with tert-butyl hydroperoxide and the catalytic hydrogenation are carried out in a tert-butanol solvent.

6. The process of claim 5 wherein the hydrogenation catalyst is Raney nickel.

7. The process of claim 1 wherein the unreduced cobalt on silica catalyst contains at least 20% by weight of cobalt.

8. The process of claim 6 wherein the unreduced cobalt on silica catalyst contains at least 20% by weight of cobalt.

9. The process of claim 1 wherein the reaction of 1,3-butadiene with tert-butyl hydroperoxide is carried out at temperatures of from −20° to +25° C.

10. The process of claim 8 wherein the reaction of 1,3-butadiene with tert-butyl hydroperoxide is carried out at temperatures of from −20° to +25° C.

11. The process of claim 1 wherein the unreduced cobalt on silica catalyst is present in an amount such that the molar ratio of cobalt to tert-butyl hydroperoxide is from 0.001 to 0.1.